United States Patent [19]

Storz

[11] Patent Number: 4,574,803

[45] Date of Patent: Mar. 11, 1986

[54] TISSUE CUTTER

[76] Inventor: Karl Storz, Postfach 400, Mittlestrasse 8, Tuttlingen, Fed. Rep. of Germany

[21] Appl. No.: 234,474

[22] Filed: Feb. 17, 1981

Related U.S. Application Data

[63] Continuation of Ser. No. 4,815, Jan. 19, 1979, abandoned.

[51] Int. Cl.$^4$ .............................................. A61B 17/32
[52] U.S. Cl. ................................................... 128/305
[58] Field of Search .............................. 128/751–755, 128/305

[56] References Cited

U.S. PATENT DOCUMENTS 3,692,020 9/1972 Schied .................................. 128/755
3,989,033 11/1976 Halpern et al. ...................... 128/754

FOREIGN PATENT DOCUMENTS 1215439 12/1970 United Kingdom ................ 128/752

Primary Examiner—Michael H. Thaler
Attorney, Agent, or Firm—Donald D. Mon

[57] ABSTRACT

A tissue cutter with forceps-like handles at its proximal end for actuating the cutter. The cutter includes a tube to receive cut-off pieces of tissue. A stripper strips the pieces of tissue from a cutting tool. A stripper rod, which is spring-loaded and subject to being locked and released moves the tissue into the tube, this operation being accomplished by completion of a cutting sequence.

6 Claims, 6 Drawing Figures

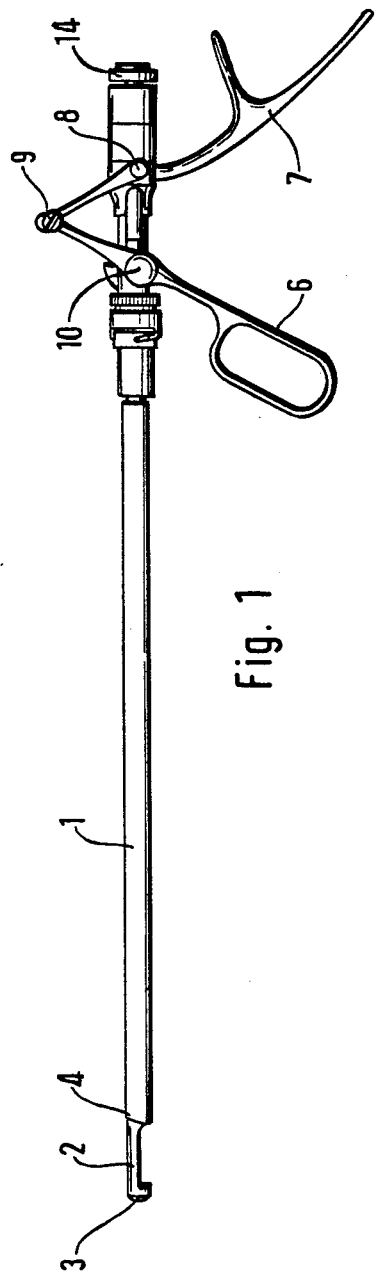
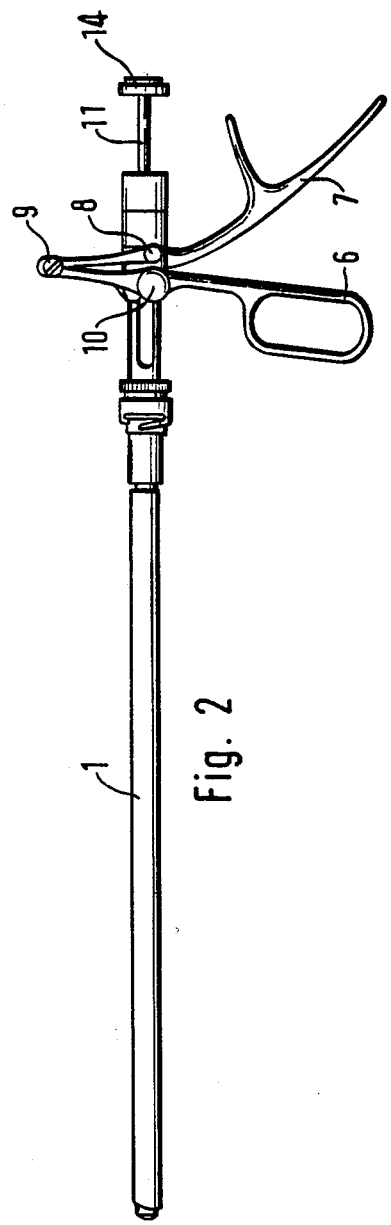

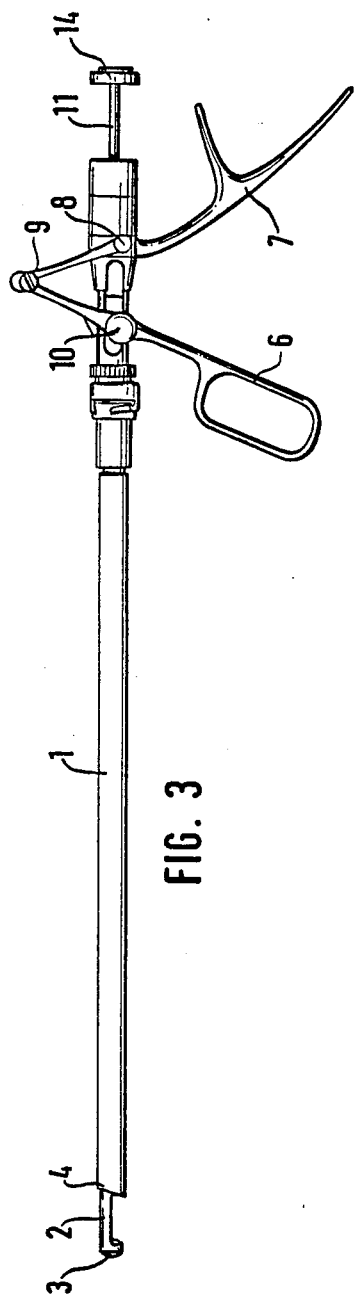
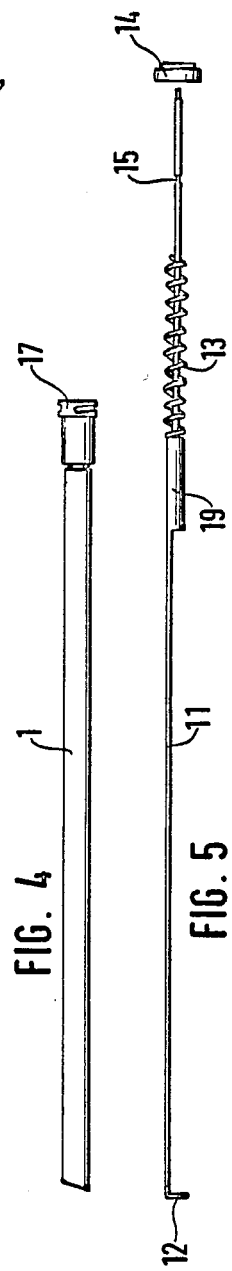
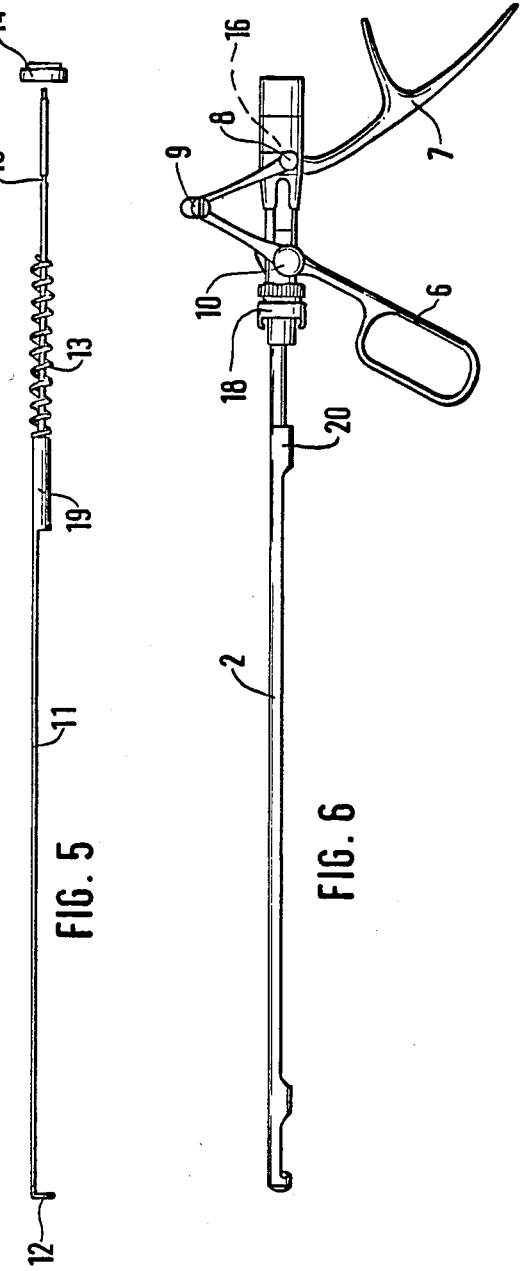
FIG. 3  FIG. 4  FIG. 5  FIG. 6

TISSUE CUTTER

CROSS-REFERENCE TO OTHER APPLICATION

This is a continuation of applicant's co-pending U.S. patent application Ser. No. 004,815, filed Jan. 19, 1979, now abandoned.

BACKGROUND OF THE INVENTION

The invention relates to a tissue cutter for medical purposes with forceps-like handles at the proximal end for actuating the cutting tool at the distal end by means of an outer shaft and an operating rod, whereby the outer shaft of the tissue cutter is constructed in tubular manner and internally at the distal end has a stripper for stripping the drawn-in pieces of tissue from the cutting tool.

For the purpose of removing the cut tissue or pieces of bone from the instrument it was hitherto necessary to remove the instrument from the operating area after each cut, which is not only very time-consuming, but also very unpleasant for the patient. Particularly in laparoscopy the length of the operation was considerably increased by the frequent removal of the tissue cutter. The present tissue cutter has the important advantage relative thereto that there is no need for the frequent removal thereof for the purpose of removing cut tissue or bones. For this purpose the pieces of tissue are moved into the tubular shaft and are held there by the stripper by cross-sectionally saw tooth-shaped recesses in the inner wall of the shaft. Generally the endoscope shaft is sufficiently long to receive all pieces of tissue and bone resulting from an operation (German Utility Model 7 705 342).

However, it may occur, particularly at the start of the operation, that specimens do not remain in the endoscope shaft and instead are displaced forwards together with the cutting tool, i.e. they remain attached to the latter. This is for example due to the fact that the pieces are only very small and cannot therefore be forced with the desired pressure into the shaft.

It is also due to the fact that as a result of the adhesive power such small pieces of tissue adhere to the cutting tool.

BRIEF SUMMARY OF THE INVENTION

The problem of the invention is to obviate the above disadvantage and ensure that in all cases the specimens remain in the area of the shaft end, in particular through being reliably detached from the cutting tool.

According to the invention this problem is solved by the tissue cutter of the type indicated hereinbefore. A stripper rod with a stripper at the distal end is arranged within the cutting tool and is loaded by a spring, and a locking mechanism is provided for releasing the spring-loaded stripper rod when the latter has reached its outermost distal position.

Thus, by means of the stripper rod according to the invention and the stripping tool located thereon the specimen is in all cases removed from the cutting tool. When the cutting tool is displaced forwards again the specimen is held in its proximal position within the endoscope shaft by the stripper tool. Only when the cutting tool has reached its outermost distal position again is the stripper rod according to the invention moved in percussive manner forwards by the spring, so that due to its inertia alone the specimen remains in the shaft, i.e. it is detached from the stripper tool.

According to a further development of the invention the stripper is constructed as a disc at right angles to the direction of movement.

The size of the disc is naturally adapted to the internal diameter of the outer shaft, so that it is ensured that all specimens are held back in the shaft.

It is also very advantageous for the stripper rod to be provided with a catch for engaging a spring-loaded stop member at the proximal end.

The catch can be used to connect or disconnect the stripper rod and the instrument, when the cutting tool is in its outermost distal position.

BRIEF DESCRIPTION OF THE DRAWINGS

Further advantages and details of the invention can be gathered from the following description of an embodiment with reference to the drawings, wherein:

FIG. 1 is a side view of the tissue cutter with extended cutting tool and stripper;

FIG. 2 is like FIG. 1 but with retracted cutting tool and stripper;

FIG. 3 is like FIG. 1, but the stripper rod and the stripper are still in the proximal position;

FIG. 4 is a side view of the outer shaft only;

FIG. 5 is a side view of the stripper rod with the stripper and spring; and

FIG. 6 is a side view of the operating rod of the cutting tool and the remaining parts, without the parts according to FIGS. 4 and 5.

DETAILED DESCRIPTION OF THE PREFERRED EMBODIMENTS

FIG. 1 shows the complete instrument in the assembled state with the two forceps-like handles 6 and 7 at the proximal end. Handle 7 can be pivoted about articulation 8, whilst handle 6 with its fulcrum point 10 is movable in the longitudinal direction of the instrument and is pivotable about articulation 9. Articulation 10 is connected in articulated manner with the operating rod 2 within the endoscope shaft 1. As can be seen at the left at the distal end of the instrument the operating rod 2 is fixedly connected with tool 3.

If handle 6 is now moved to the right with respect to handle 7, the operating rod 2 and tool 3 can be moved backwards and forwards in the shaft 1 until tool 3 is completely within shaft 1, as shown in FIG. 2. The distal end 4 of shaft 1 is constructed as a counter-tool for cutting tool 3. In addition, it is provided with a stripper having cross-sectionally saw tooth-shaped recesses, which act in the manner of barbs. Thus, the cut pieces of tissue can easily slide through from left to right, but are prevented from passing in the opposite direction together with tool 3 to the front again into the position shown in FIGS. 1 and 3 by the above-mentioned recesses. This is not shown in detail because the hitherto described tissue cutter forms part of the prior art.

According to the invention additionally a stripper rod 11 with a stripper 12 is provided in axially movable manner at the distal end within operating rod 2, of also FIGS. 5 and 6. It can be gathered from FIGS. 1 and 2 that through the movement of handle 6 to the right stripper rod 11 together with operating rod 2 are moved to the right to the distal end.

FIG. 3 now shows that this position according to FIG. 2 is retained, although operating rod 2 with tool 3 has been moved forwards again to the distal end. This is due to the fact that stripper rod 11 with its catch 15 has engaged in a spring-loaded stop member 16 in the area of articulation 8 in FIG. 2, and does not therefore effect the following axial forwards movement of operating rod 2.

FIGS. 4, 5 and 6 show details of the subject matter of the invention. Shaft 1 according to FIG. 4 is provided in conventional manner with a bayonet catch 17, which is released by the corresponding counterpiece 18 according to FIG. 6. In addition stripper rod 11 has been removed from its mounting support within operating rod 2. Thus, rod 11 when in the mounted state is axially movable with respect to operating rod 2.

To the left in FIG. 5 is is possible to see stripper 12, constructed in the form of a disc, at right angles to the axial direction of movement. The abutment 19 for spring 13 is located in the centre of rod 11. Further to the right it is possible to see the above-mentioned catch 15 and finally stripper rod 11 is terminated at the distal end by a disc 14.

The subject matter of the invention will be explained hereinafter.

In the mounted state stripper rod 11 is located in its axially movable position within the operating rod 2. If handle 6 is moved to the right according to FIG. 2, then shoulder 20 of operating rod 2 moves stripper rod 11 together with operating rod 2 to the right, so that the stripper rod is retracted in accordance with FIG. 2. Spring 13 is compressed, so that operating rod 2 is spring-loaded in the axial direction. At the end of the working traverse, rod 11 with its catch 15 engages in the proximal end 16 of the instrument, where there is a corresponding, not shown locking mechanism. Spring-loaded members of this type are known, so that no detailed description is necessary here.

If handle 6 is now moved forwards according to FIG. 3, rod 11 remains in the indicated position. Only when cutting tool 3 has reached the furthest forward position is it possible to release the stop member 16 from catch 15 either manually or by operating handle 6, so that now the rod is moved abruptly in a percussive manner to the left by spring 13 until it comes to rest in the position of FIG. 1.

Thus, no additional actuation by the doctor is necessary. As a result of this percussive operation the disc-like stripper 12 is detached from the specimen which consequently remains at the distal end 4 of outer shaft 1. In the case of a plurality of successive actuations the various specimens are introduced successively into the outer shaft 1 by cutting tool 3 together with stripper 12.

The invention is not restricted to the represented embodiment. The general spatial concept comprises providing a stripper 12 with stripper rod 11 which, by means of the arrangement of spring 13 and locking mechanism 15, can be displaced forwards in percussive manner, so that the disc-like stripper 12 is reliably released from the specimen and the latter does not continue to adhere to it.

What is claimed is:

1. A tissue cutter for surgical purposes, said tissue cutter having a proximal and a distal end, and comprising:
   a support;
   an outer tube mounted to said support having a central axis, an internal axially extending passage, and a first cutter blade at its distal end;
   an operating rod in said passage and axially reciprocable therein;
   a second cutter blade carried by said operating rod and reciprocable thereby, whereby in one axial position of said rod said second cutter blade projects distally beyond said first cutter blade, and in another axial position it is drawn into said passage, having made a close tissue-cutting pass through said first cutter blade so as to cut tissue disposed between them;
   a stripper rod in said passage and axially reciprocable therein, said stripper rod being adapted to be moved into said outer tube when said second cutter blade is moved into said outer tube, and selectively to remain in said outer tube when said second cutter blade is moved out of said outer tube;
   a stripper carried by said stripper rod and its distal end, adapted either to be outside of said outer tube or to be inside of said outer tube when said first cutter blade is outside said tube and to move tissue cut by said blades into said passage;
   bias means biasing said stripper rod toward a position where said stripper is outside of said outer tube;
   releasable latch means for restraining said stripper rod with said stripper inside said outer tube in opposition to said bias means; and
   handle means pivotally mounted to said support for reciprocating said operating rod, said operating rod and stripper rod occupying less than the total cross-section of said passage near its distal end, whereby to receive plural cuttings of tissue, whereby when said operating rod is moved toward the proximal end and the cutters pass one another, a tissue cutting is moved into said outer tube by said stripper, and said stripper rod is latched so that the stripper is inside said outer tube, after which said handle means can be moved to permit said first cutter to return to its most distal position, release of said latch means enabling said stripper rod to be moved abruptly by said bias means in the distal direction to leave said tissue cutting inside said outer tube at a location spaced from said distal end of said outer tube as a consequence of the inertia of said tissue cutting.

2. A tissue cutter according to claim 1 in which said stripper is a disc at right angles to said axis.

3. A tissue cutter according to claim 1 in which said latch means includes a catch on said stripper rod.

4. A tissue cutter according to claim 1 in which said handle includes articulation means connected to said support and to said operating rod.

5. A tissue cutter according to claim 4 in which said stripper is a disc at right angles to said axis.

6. A tissue cutter according to claim 5 in which said latch means includes a catch on said stripper rod.

* * * * *